US00PP15026P2

(12) United States Plant Patent
Jin

(10) Patent No.: US PP15,026 P2
(45) Date of Patent: Jul. 20, 2004

(54) IXORA PLANT NAMED 'PINK PIXIE'

(50) Latin Name: *Ixora chinensis*
Varietal Denomination: Pink Pixie

(75) Inventor: Tjoe Foeng Jin, Bogor (ID)

(73) Assignee: Bloomin' Good, Inc., Homestead, FL (US)

( * ) Notice: Subject to any disclaimer, the term of this patent is extended or adjusted under 35 U.S.C. 154(b) by 0 days.

(21) Appl. No.: 10/716,017

(22) Filed: Nov. 18, 2003

(51) Int. Cl.[7] ..... A01H 5/00
(52) U.S. Cl. ..... Plt./226
(58) Field of Search ..... Plt./226

*Primary Examiner*—Kent Bell
(74) *Attorney, Agent, or Firm*—C. A Whealy

(57) ABSTRACT

A new and distinct cultivar of Ixora plant named 'Pink Pixie', characterized by its compact, upright and mounded plant habit; freely branching habit and relatively short internodes; dense and bushy growth habit; dark green-colored leaves; and large inflorescences with numerous bright pink-colored flowers.

2 Drawing Sheets

Botanical classification/cultivar designation: *Ixora chinensis* cultivar Pink Pixie.

BACKGROUND OF THE INVENTION

The present Invention relates to a new and distinct cultivar of Ixora plant, botanically known as *Ixora chinensis*, and hereinafter referred to by the name 'Pink Pixie'.

The new Ixora was discovered by the Inventor on Jan. 1, 1996 as a naturally-occurring branch mutation of the *Ixora chinensis* cultivar Rosey Pink, not patented, in a controlled environment in Bogor, Indonesia. The new Ixora was selected by the Inventor on the basis of its unique flower color.

Asexual reproduction of the new cultivar by terminal cuttings taken in a controlled environment in Bogor, Indonesia, since Jan. 1, 1996, has shown that the unique features of this new Ixora are stable and reproduced true to type in successive generations of asexual reproduction.

SUMMARY OF THE INVENTION

The following traits have been repeatedly observed and are determined to be the unique characteristics of 'Pink Pixie'. These characteristics in combination distinguish 'Pink Pixie' as a new and distinct cultivar:

1. Compact, upright and mounded plant habit.
2. Freely branching habit and relatively short internodes; dense and bushy growth habit.
3. Dark green-colored leaves.
4. Large inflorescences with numerous bright pink-colored flowers.

Plants of the new Ixora differ from plants of the parent, the cultivar Rosey Pink, in the following characteristics:

1. Plants of the new Ixora are shorter than plants of the cultivar Rosey Pink.
2. Plants of the new Ixora have shorter internodes, are more freely branching and are denser and bushier than plants of the cultivar Rosey Pink.
3. Plants of the new Ixora have smaller leaves than plants of the cultivar Rosey Pink.

4. Plants of the new Ixora are more floriferous than plants of the cultivar Rosey Pink.
5. Plants of the new Ixora have larger inflorescences than plants of the cultivar Rosey Pink.

Plants of the new Ixora can be compared to plants of the cultivar Nora Grant, not patented. In side-by-side comparisons conducted in Bogor, Indonesia, plants of the new Ixora differed primarily from plants of the cultivar Nora Grant in the following characteristics:

1. Plants of the new Ixora were more compact than plants of the cultivar Nora Grant.
2. Plants of the new Ixora had smaller leaves than plants of the cultivar Nora Grant.
3. Flower color of plants of the new Ixora was lighter pink than flower color of plants of the cultivar Nora Grant.
4. Plants of the new Ixora flowered under low light (semi-shade) conditions whereas plants of the cultivar Nora Grant required full sun conditions to flower.

Plants of the new Ixora can also be compared to plants of the cultivar Petite Pink, not patented. In side-by-side comparisons conducted in Bogor, Indonesia, plants of the new Ixora differed primarily from plants of the cultivar Petite Pink in the following characteristics:

1. Plants of the new Ixora had a more open plant habit than plants of the cultivar Petite Pink.
2. Plants of the new Ixora had larger leaves than plants of the cultivar Petite Pink.
3. Plants of the new Ixora flowered under low light (semi-shade) conditions whereas plants of the cultivar Petite Pink required full sun conditions to flower.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photograph differ slightly from the color values cited in the detailed botanical description which accurately describe the colors of the new Ixora.

The photograph on the first sheet comprises a side perspective view of a typical flowering plant of 'Pink Pixie' grown in a container.

The photograph on the second sheet is a close-up view of typical inflorescences and leaves of 'Pink Pixie'.

DETAILED BOTANICAL DESCRIPTION

The cultivar Pink Pixie has not been observed under all possible environmental conditions. The phenotype may vary somewhat with variations in environment such as temperature and light intensity without, however, any variance in genotype. The aforementioned photographs and following observations and measurements describe plants grown in Homestead, Fla., under commercial practice in a polypropylene-covered shadehouse that provided a 30% light reduction. During the production of the plants, day temperatures averaged 32° C. and night temperatures averaged 24° C. Cuttings were planted in 25-cm containers and grown for about six months. In the following description, color references are made to The Royal Horticultural Society Colour Chart, 1995 Edition, except where general terms of ordinary dictionary significance are used.

Botanical classification: *Ixora chinensis* cultivar Pink Pixie.

Parentage: Naturally-occurring branch mutation of the *Ixora chinensis* cultivar Rosey Pink, not patented.

Propagation:

*Type cutting*.—Terminal cuttings.

*Time to initiate roots, summer*.—About 20 days at 29° C.

*Time to initiate roots, winter*.—About 50 days at 18° C.

*Time to produce a rooted cutting or liner, summer*.—About 40 days at 29° C.

*Time to produce a rooted cutting or liner, winter*.—About 75 days at 16 to 18° C.

*Root description*.—Fibrous; white in color becoming dark brown with development.

*Rooting habit*.—Freely branching; dense.

Plant description:

*Form*.—Compact, upright and mounded plant habit.

*Growth and branching habit*.—Vigorous and freely-branching with lateral branches potentially developing at every node after pinching; relatively short internodes, dense and bushy growth.

*Plant height*.—About 25 to 30 cm.

*Plant diameter or spread*.—About 30 to 40 cm.

*Lateral branches*.—Internode length: About 0.5 to 3.5 cm. Texture: Smooth, glabrous. Color: 146A; with development, becoming woody and tinged with 197A.

*Foliage description*.—Arrangement: Opposite, simple. Length: About 4 to 5 cm. Width: About 1.5 to 2.4 cm. Shape: Ovate. Apex: Acute. Base: Acute to attenuate. Margin: Entire. Texture, upper and lower surfaces: Smooth, glabrous. Venation pattern: Pinnate. Color: Developing foliage, upper surface: 146A; midrib, 146D; lateral veins, 146A. Developing foliage, lower surface: 146B; midrib, 146D; lateral veins, 146B. Fully expanded foliage, upper surface: 137A; midrib, 146B; lateral veins, 137A; shiny to glossy. Fully expanded foliage, lower surface: 146B; midrib, 146D; lateral veins, 146B. Petiole: Length: About 3 mm. Diameter: About 2 mm. Texture, upper and lower surfaces: Smooth, glabrous. Color: 146D.

Flower description:

*Flower type and habit*.—Numerous single salverform gamopetalous flowers arranged on crowded branched terminal corymbs; inflorescences compact and globose. Freely flowering with about 75 to 120 flowers and flower buds per inflorescence. Inflorescences positioned above and beyond the foliage. Flowers not fragrant.

*Flowering season*.—Plants of the new Ixora flower year round in Florida; peak flowering occurring during the summer months.

*Flower longevity*.—Flowers last about five days on the plant before fading; inflorescences last about four weeks. Flowers not persistent.

*Inflorescence diameter*.—About 6 to 9 cm.

*Flower size*.—Diameter: About 1.5 cm. Lobe width: About 4 mm. Tube length: About 2.9 cm. Tube diameter: About 0.5 mm.

*Flower buds color*.—67D.

*Petals*.—Quantity/arrangement: Four per flower fused at base. Shape, lobes: Roughly elliptic. Apex: Acute. Margin: Entire. Texture, upper and lower surfaces: Smooth, glabrous. Color: Upper surface: 67D, becoming closer to 65B to 65C with development. Lower surface: 68C, becoming closer to 65B to 65C with development Tube: 67D tinged with 146D, becoming closer to 145B with development.

*Sepals*.—Quantity/arrangement: Four, fused into a tube; inconspicuous. Length: About 2 mm. Diameter: About 1 mm. Shape: Triangular. Apex: Acute. Margin: Entire. Texture, upper and lower surfaces: Smooth, glabrous. Color, upper and lower surfaces: 146B.

*Reproductive organs*.—Stamens: Quantity/arrangement: Four, affixed to junction of the tube and lobes. Anther shape: Oblong. Anther size: About 1 mm by 0.2 mm. Anther color: 22C. Pollen amount: None observed. Pistils: Quantity: One. Stigma shape: Bifurcate. Stigma size: About 0.5 mm by 0.2 mm. Stigma color: 63D with 64C. Style length: About 2.9 cm. Style diameter: About 0.1 mm. Style color: 150D. Ovary position: Inferior. Ovary diameter: About 0.2 mm. Ovary color: 146D.

*Fruit/seed*.—Fruit and seed production has not been observed.

Disease/pest resistance: Plants of the new Ixora have not been observed to be resistant to pathogens and pests common to Ixora.

Weather tolerance: Plants of the new Ixora have been observed to be tolerant to rain, wind and temperatures ranging from 2 to 35° C.

It is claimed:

1. A new and distinct cultivar of Ixora plant named 'Pink Pixie', as illustrated and described.

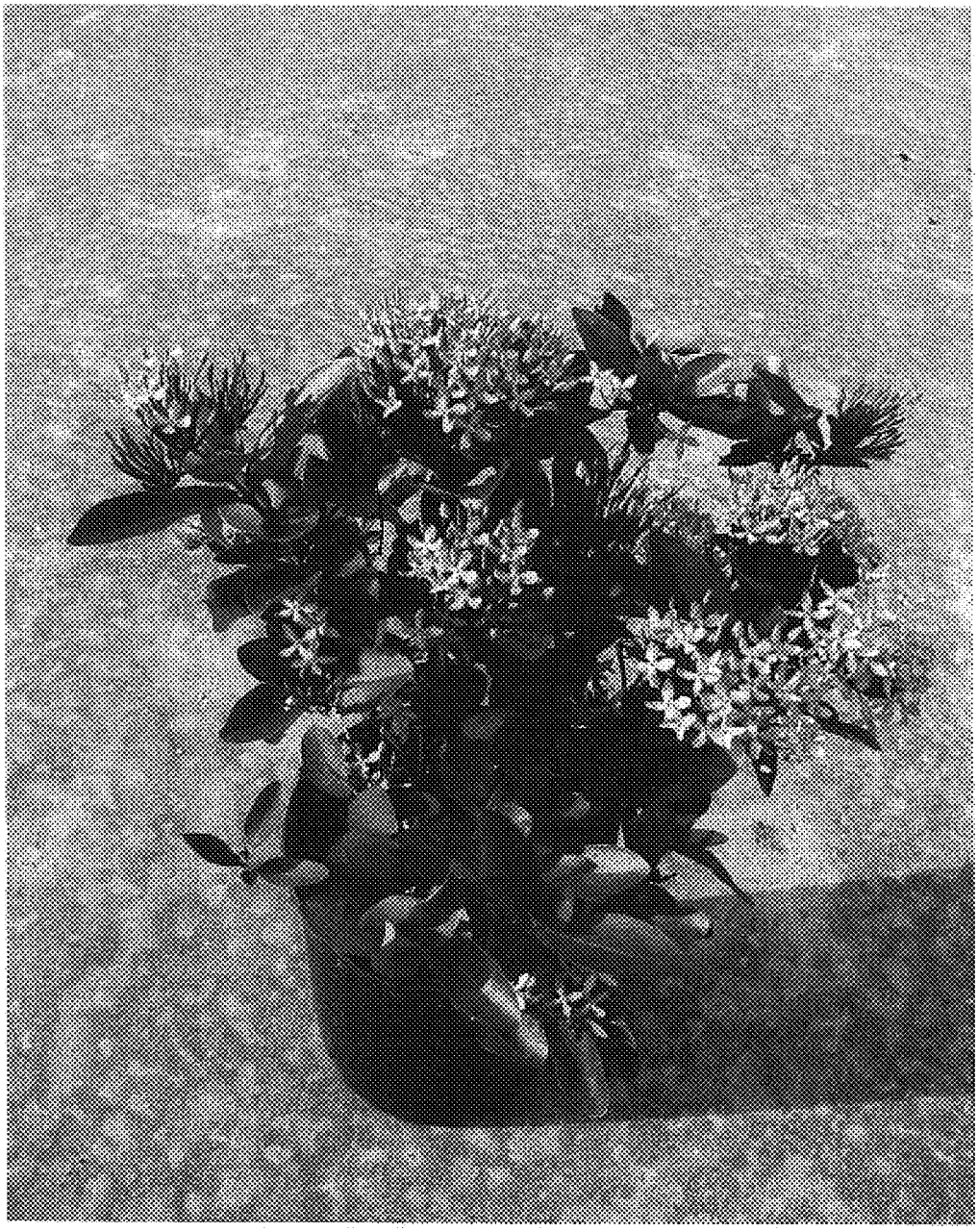

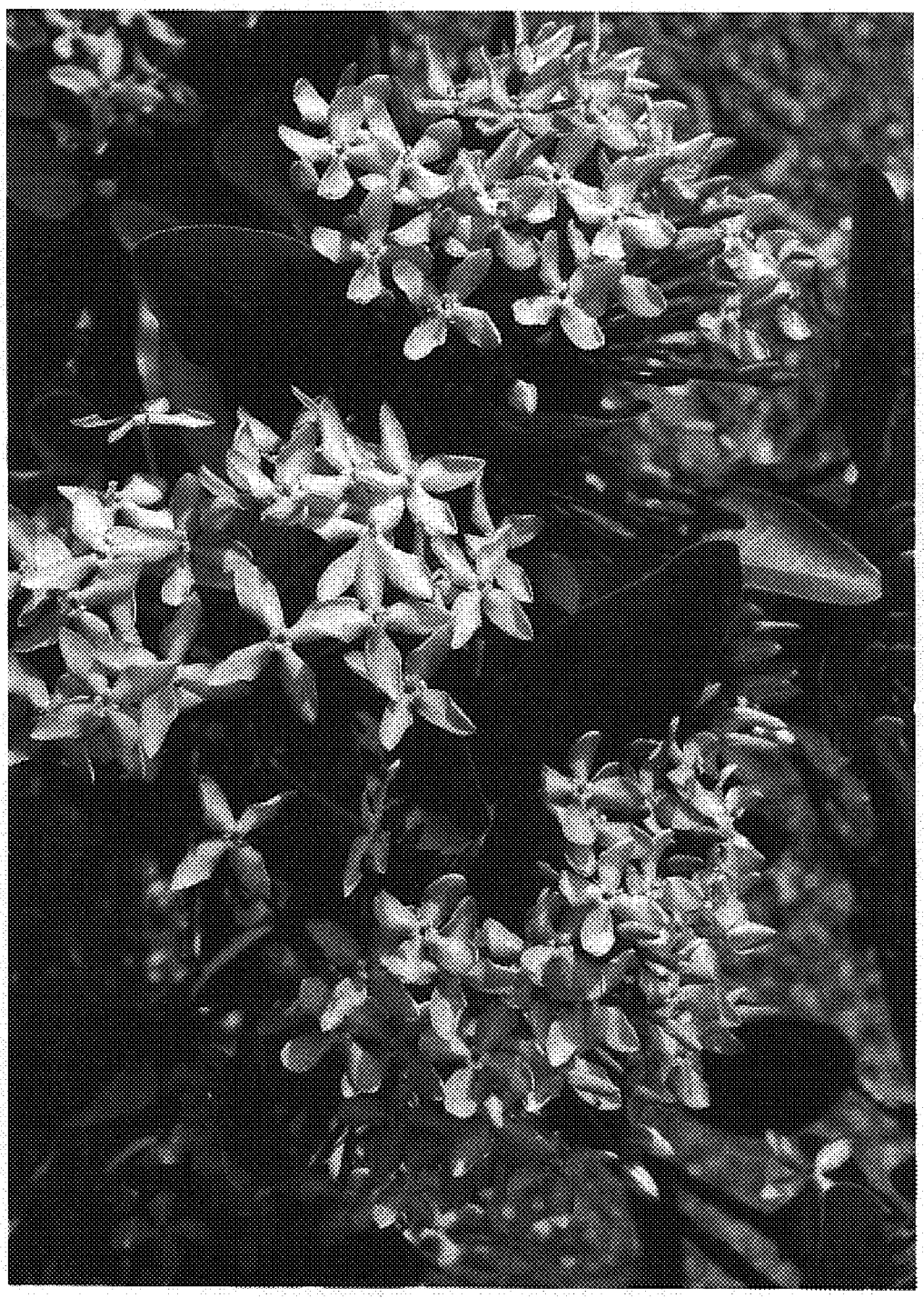

* * * * *